United States Patent [19]
Wieselman et al.

[11] Patent Number: 5,869,071
[45] Date of Patent: Feb. 9, 1999

[54] ONE-STEP SKIN CLEANING COMPOSITION AND SKIN TREATMENT METHOD FOR INCONTINENT DERMATITIS

[75] Inventors: Jerome J. Wieselman; Steven M. Wieselman, both of St. Louis, Mo.

[73] Assignee: B & G Labs, Inc., St. Louis, Mo.

[21] Appl. No.: 745,094

[22] Filed: Nov. 7, 1996

[51] Int. Cl.$^6$ .............................. A61K 6/00; A61K 7/00; A01N 25/34
[52] U.S. Cl. ............................. 424/401; 424/404
[58] Field of Search ............................. 514/855; 424/401

[56] References Cited

U.S. PATENT DOCUMENTS

| | | | |
|---|---|---|---|
| 3,829,563 | 8/1974 | Barry et al. | 424/168 |
| 3,852,475 | 12/1974 | Tarangul | 424/361 |
| 3,919,430 | 11/1975 | Siegel | 424/365 |
| 4,035,514 | 7/1977 | Davis | 424/365 |
| 4,389,418 | 6/1983 | Burton | 424/365 |
| 4,495,079 | 1/1985 | Good | 252/106 |
| 4,599,340 | 7/1986 | Silver et al. | 514/277 |
| 4,808,322 | 2/1989 | McLaughlin | 252/121 |
| 4,832,858 | 5/1989 | Vashnupad et al. | 252/49.5 |
| 4,941,990 | 7/1990 | McLaughlin | 252/121 |
| 4,980,084 | 12/1990 | Vishnupad et al. | 252/309 |
| 4,981,677 | 1/1991 | Thau | 424/43 |
| 5,013,763 | 5/1991 | Tubesing et al. | 514/772 |
| 5,110,593 | 5/1992 | Benford | 424/401 |
| 5,196,405 | 3/1993 | Packman | 514/53 |
| 5,308,526 | 5/1994 | Dias et al. | 252/125 |
| 5,312,559 | 5/1994 | Kacher et al. | 252/125 |
| 5,387,417 | 2/1995 | Rentsch | 424/401 |
| 5,409,691 | 4/1995 | Swain | 424/49 |
| 5,478,814 | 12/1995 | Packman | 514/53 |
| 5,489,576 | 2/1996 | Yoshida et al. | 514/28 |
| 5,496,488 | 3/1996 | Kacher et al. | 252/125 |
| 5,504,117 | 4/1996 | Gorfine | 514/742 |
| 5,525,345 | 6/1996 | Warner et al. | 424/402 |

*Primary Examiner*—Thurman K. Page
*Assistant Examiner*—Sharon Howard
*Attorney, Agent, or Firm*—Blackwell Sanders Peper Martin

[57] ABSTRACT

A composition for use with incontinent patients that cleanses the peritoneum, moisturizes and leaves a protective barrier against wetness and irritants, wherein the composition uses petrolatum as the barrier material. A method of using the above composition to cleanse, moisturize and provide a protective petrolatum barrier in one step.

19 Claims, No Drawings

ONE-STEP SKIN CLEANING COMPOSITION AND SKIN TREATMENT METHOD FOR INCONTINENT DERMATITIS

FIELD OF THE INVENTION

This invention relates to a composition for use with incontinent patients that cleanses the peritoneum, moisturizes and leaves a protective barrier against wetness and irritants. The composition uses petrolatum as the barrier material. This invention further provides a method of using the above composition to cleanse, moisturize and provide a protective petrolatum barrier in one step.

BACKGROUND OF THE INVENTION

Dermatitis is a common problem for incontinent patients. There are three basic products which are used to treat incontinent dermatitis: cleansers, moisturizers and barrier products, and various combinations of these products. Most cleansers involve the steps of wetting the skin, applying the cleanser, removing the cleanser and matter, rinsing and drying. Additional steps can include the application of moisturizers and/or barrier products.

Some cleansers are applied and wiped away in one step, leaving a type of moisturizer and barrier product. Such products include Promise Skin Caring Wash Cream, Hollister Restore Clean-N-Moist No Rinse Breathable Barrier, and MPM Cleansing Barrier Foam. These products have the advantage of providing a product that cleanses, moisturizes and provides a type of barrier in one step.

None of the above products, however, use petrolatum as the barrier product. The barrier products typically used are silicones or polymeric products which generally have inferior barrier properties. A superior barrier product is petrolatum. However, petrolatum has several properties that make it difficult to use. Petrolatum, when applied to the skin, is greasy and has unacceptable tactile properties. Attempts have been made to emulsify petrolatum in a cream or lotion form in order to reduce its greasy feel when applied to the skin, or to make it washable, as in U.S Pat. Nos. 4,389,418, 4,832,858 and 4,980,084. A foam skin conditioner containing petrolatum is disclosed in U.S. Pat. No. 4,981,677.

Cleansers containing petrolatum are disclosed in U.S. Pat. Nos. 3,829,563, 5,308,526, 5,312,559 and 5,496,488. These cleansers, however, are conventional cleansers that employ wetting, lathering, rinsing and drying. They are distinctly different from the claimed composition that involves one-step cleansing, e.g., applying the cleanser to the peritoneum and then wiping it dry, leaving a petrolatum barrier product on the skin.

U.S. Pat. No. 5,110,593 discloses an ointment applied to a patient having diaper rash or incontinent dermatitis, wherein the ointment is applied to the peritoneum after cleaning and drying, and the ointment contains petrolatum, lanolin, oxyquinoline to inhibit bacterial growth, and other additives.

None of the above references disclose the present composition for use with incontinent patients that cleanses, moisturizes and leaves a protective petrolatum barrier against wetness and irritants in one step. Further, none of the above references disclose the present composition that can be conveniently applied as a dispersing spray.

SUMMARY OF THE INVENTION

The present invention relates to a composition for cleaning the peritoneum in one step comprising an emulsion of:

(a) from about 10 to 75 weight % water,
(b) from about 10 to 50 weight % petrolatum,
(c) from about 5 to 25 weight % surface active detergent,
(d) from about 1 to 10 weight % emulsifying agent,
(e) from about 0 to 10 weight % humectant, and
(f) from about 0 to 10 weight % silicone, and wherein the composition cleanses, moisturizes and leaves a protective barrier of petrolatum against wetness and irritants.

A method for cleansing the peritoneum comprising:

(1) applying to the peritoneum an emulsion comprising:
  (a) from about 10 to 75 weight % water,
  (b) from about 10 to 50 weight % petrolatum,
  (c) from about 5 to 25 weight % surface active detergent,
  (d) from about 1 to 10 weight % emulsifying agent,
  (e) from about 0 to 10 weight % humectant, and
  (f) from about 0 to 10 weight % silicone, and
(2) wiping the emulsion from the peritoneum, thereby cleansing, moisturizing and leaving petrolatum as a protective barrier against wetness in one step.

DETAILED DESCRIPTION OF THE INVENTION

The present composition is an emulsion of water and petrolatum. The petrolatum (or petroleum jelly) useful in the present invention can be any grade of petrolatum recognized in the art as suitable for human application, and is present in the composition in the range about of 10 to 50 weight %. Less than about 10 weight % of petrolatum may yield a composition that provides an ineffective barrier against wetness and irritants. Greater than about 50 weight % may yield a composition that is not easily applied and has a reduced cleaning capability. The preferred amount of petrolatum is from about 15 to 35 weight % of the composition.

The composition has from about 5 to 25 weight % of a surface active detergent. The surface active detergent utilized in the present composition may be of the anionic, non-ionic or amphoteric types, or a combination thereof. An important consideration in the selection of a suitable detergent ingredient is the relative irritant properties of the detergent. Examples of suitable detergents include the following:

Anionic: aklyl sulfates, alkyl ether sulfates, alkyl benzene sulfonates, alkanolamides, amine oxides, alpha olefin sulfonate, betaines, sarcosinates, sulfoacetates, sulfosuccinates, cocoamphocarboxy glycinate, alkali and triethanolamine lauryl sulfates, lauryl ether sulfates, sodium alkylbenzene sulfonate, secondary alkyl sulfates, salts of higher acyl esters of isethionic acid, sodium salts of higher acyl derivatives of taurine or methyl taurine, alkyl phenol polyether sulfates, higher acyl derivatives of glycine and methylglycine, di-higher alkyl sulfosuccinates, higher alkyl alkanolamine ester sulfosuccinates, higher alkyl monoglyceride sulfates, alpha-olefin sulfonates.

Nonionic: alkyl aryl polyether alcohols, alpha-hydro-omega-hydroxy-poly(oxypropylene)polyoxyethylene block copolymers; and Amphoteric: disodium salts of higher alkyl substituted imidazolinium dicarboxylic acids wherein the connecting group liking said carboxyl groups to the imidazolinium ring contains an ether linkage, higher acyl beta-aminopropionates, higher acyl peptides, higher alkyl amino betaines, and the like.

The preferred surface active detergent is a combination of triethanolamine lauryl sulfate and cocoamphocarboxy glycinate. The preferred amount in the composition of triethanol amine lauryl sulfate is in the range of 2 to 10 weight %, and the preferred amount of cocoamphocarboxy glycinate is in the range of about 2 to 10 weight %. The preferred total amount of surface active detergent is in the range of about 8 to 15 weight % of the composition. If the amount of surface active detergent is less than about 5 weight %, there may be insufficient cleaning. If the amount of surface active detergent is greater than about 25 weight %, the emulsion may break down, and there may be greater irritation.

Emulsifiers are present in the composition in the range of about 1 and 10 weight %. The emulsifiers increase the stability of the emulsion and increase the cleaning capability. A variety of emulsifiers may be used in the emulsion and may consist of a single emulsifying agent, or a mixture of several emulsifying agents. An emulsifier is a molecule that combines a hydrophilic (water-loving or polar) group with a lipophilic (oil-loving or non-polar) group.

The emulsifiers of the present invention include sorbitan fatty acid esters, polyoxyethylene sorbitan fatty acid esters, polyoxyethylene sorbitol esters of fatty acids and tallow acids, polyoxyethylene fatty acid esters, polyoxyethylene fatty alcohol ethers, polypropylene glycol fatty acid esters, fatty alcohol phosphate esters, polyethoxylated fatty alcohol phosphate esters and the like. The preferred emulsifiers include cetyl alcohol, stearyl alcohol, stearic acid, palmitic acid, glyceryl monostearate, glyceryl monopalmitate, Carbomer 934 and 940, an emulsifier sold by B. F. Goodrich, behentrimonium methosulfate (a quaternary amine emulsifier sold by Croda Co.) and glyceryl monolaurate.

The preferred emulsifier is a combination of behentrimonium methosulfate, stearyl alcohol, cetyl alcohol and glyceryl monolaurate. Less than about 1 weight % of emulsifier in the composition causes the emulsion to break down. Greater than about 10 weight % of the emulsion in the composition increases the viscosity such that the emulsion is difficult to pour or handle.

The most preferred composition has from about 0.25 to 1.0 weight % behentrimonium methosulfate, from about 0.25 to 1.0 weight % cetyl alcohol, from about 0.25 to 1.0 weight % stearyl alcohol, and from about 1.0 to 3.0 weight % glyceryl monolaurate.

The humectant is optional, though preferred, and is present in the composition in the range of about 1 to 10 weight %. The humectant is typical of those used in skin care products. Examples of suitable humectants include glycerine, propylene glycol, sorbitol, sucrose, and the alkali metal salts of pyrrolidone carboxylic acid. The most preferred humectant is propylene glycol, and is present in the range of about 0.5 to 2.0 weight %.

In order to improve the lubricity of the composition during application, an optional silicone oil or fluid may be utilized, in the range of about 1 to 10 weight %. Typical silicones include dimethylpolysiloxane (CTFA name-dimethicone, a dimethyl polysiloxane endblocked with trimethyl units), diethylpolysiloxane, dimethylpolysiloxane-diphenylpolysiloxane, cyclomethicone, trimethylpolysiloxane, diphenylpolysiloxane, cetearyl dimethicone (a product of General Electric Co.) and mixtures thereof. The preferred silicone is dimethicone and is present in the composition in the range of about 3.0 to 7.0 weight %.

The pH of the composition is in the range of about 4.0 to 7.0, with the preferred range of from about 5.5 to 6.5. The acidity range matches that of healthy skin, and discourages bacterial colonization of the skin. The pH can be adjusted using any conventional buffer that is a non-irritant. The preferred buffer is citric acid.

Other conventional additives typically employed in skin care compositions may be utilized. Fragrance oils which mask the odor of the base and provide cosmetic appeal can be employed. Nontoxic and compatible dyes may be utilized to color the composition. Preservatives, such as DMDM Hydantoin (CTFA name), methylparaben or other esters of parahydroxy benzoic acid, and the ester of propylparahydroxy benzoic acid and benzethonium chloride are used. Additionally, other emollients such as aloe vera and vitamins A, D and E are used. The emulsion composition can optionally contain additional active ingredients including antimicrobial agents, antibacterial agents and antifungal agents.

The following examples are to illustrate the invention and are not to limit the scope of the claims in any manner.

EXAMPLES OF THE INVENTION

The Emulsion Composition

| | Weight % Example # | | |
|---|---|---|---|
| Component | 1 | 2 | 3 |
| Phase I | | | |
| Water | 63.00 | 72.51 | 47.51 |
| Propylene glycol | 1.00 | 1.00 | 1.00 |
| Triethanolamine laurylsulfate | 5.00 | 4.50 | 4.50 |
| Cocoamphocarboxy glycinate | 4.00 | 3.60 | 3.60 |
| Phase II | | | |
| Petrolatum | 20.00 | 10.00 | 35.00 |
| Dimethicone | 5.00 | 3.00 | 4.00 |
| Cetearyl dimethicone | 0 | 2.00 | 1.00 |
| Behentrimonium methosulfate | 0.75 | 0.75 | 0.75 |
| Glyceryl monolaurate | 0.50 | 0.50 | 0.50 |
| Cetyl alcohol | 0.75 | 0.75 | 0.75 |
| Stearyl alcohol | 0.75 | 0.75 | 0.75 |
| Phase III | | | |
| DMDM hydantoin | 0.20 | 0.20 | 0.20 |
| Benzethonium chloride | 0.02 | 0.02 | 0.02 |
| Aloe vera | 0.02 | 0.02 | 0.02 |
| Citric acid | 0.15 | 0.15 | 0.15 |
| Vitamins A, D and E in mineral oil | 0.25 | 0.25 | 0.25 |

The claimed emulsion composition is prepared as follows:

Into a steam jacketed kettle is charged phase I and heated with agitation to about 70° C.

Into a second steam jacketed kettle, phase II is charged and heated with agitation to about 70° C.

The heated ingredients of phase I are added with continuous agitation to the kettle containing phase II. The mixture is cooled to 38° C. with agitation.

The ingredients of phase III, e.g., the citric acid, aloe vera and benzethonium chloride are dissolved in equal weights of water and added to the cooled mixture. The final composition is allowed to cool for about 12 h. before packaging. The final pH is in the range of about 6.0 to 7.0. The viscosity is in the range of about 450 to 750 cps, with a preferred range of about 550 to 650 cps. The viscosity is measured by a Brookfield RVTDCP with a spindle CP-41 at 1 RPM for 3 minutes.

The emulsion composition is tested for human irritancy using the Irritection Dermal Surfactant system, a system from In Vitro International, and is found to be a non-irritant.

The emulsion composition is used to cleanse the peritoneum of patients suffering from incontinence as follows:

The emulsion composition is applied to the peritoneum by using a disposable cloth wipe saturated with the emulsion, by dispersion spraying from a bottle such as a 12 oz. bottle with a trigger sprayer, or by pouring the emulsion on a soft cleaning cloth and using the cloth to apply the emulsion. Dispersion spraying is spraying such that the spray spreads out and covers the area of an approximate circle. The peritoneum is wiped to cleanse the peritoneum, moisturize, and provide a petrolatum barrier. When the emulsion is sprayed on, a clean cloth is used to wipe the peritoneum. When the emulsion is applied with a wipe or a cloth, the wipe or cloth is used to cleanse the peritoneum. No additional rinsing is needed to cleanse the peritoneum. After cleansing is complete, a protective barrier of petrolatum is left on the peritoneum.

When it is necessary to cleanse the same patient with the emulsion composition repeatedly, it may not normally be necessary to remove the existing barrier before using the emulsion again. When the emulsion is applied a second time, the emulsion may lift the existing barrier and dissolve it. It may be wiped away, and a new barrier may be deposited on the peritoneum. The emulsion composition may make it easier to remove the previous protective barrier.

We claim:

1. A composition for cleaning the peritoneum in one step comprising an emulsion of:
   (a) from about 10 to 75 weight % water,
   (b) from about 10 to 50 weight % petrolatum,
   (c) from about 5 to 25 weight % surface active detergent,
   (d) from about 1 to 10 weight % emulsifying agent,
   (e) from about 0 to 10 weight % humectant, and
   (f) from about 0 to 10 weight % silicone, and
   wherein the composition cleanses, moisturizes and leaves a protective barrier of petrolatum against wetness and irritants.

2. The composition of claim 1, wherein the surface active detergent is a mixture of triethanolamine laurylsulfate and cocoamphocarboxy glycinate.

3. The composition of claim 1, wherein the emulsifying agent is a combination of behentrimonium metho- sulfate, cetyl alcohol, stearyl alcohol and gylceryl monolaurate.

4. The composition of claim 1, wherein the humectant is propylene glycol.

5. The composition of claim 1, wherein the silicone is dimethicone.

6. The composition of claim 1, wherein the surface active detergent is a mixture of triethanolamine laurylsulfate and cocoamphocarboxy glycinate;
   wherein the emulsifying agent is a combination of behentrimonium metho sulfate, cetyl alcohol, stearyl alcohol and gylceryl monolaurate;
   wherein the humectant is propylene glycol; and
   wherein the silicone is dimethicone.

7. A method for cleansing the peritoneum comprising:
   (1) applying to the peritoneum an emulsion comprising:
      (a) from about 10 to 75 weight % water,
      (b) from about 10 to 50 weight % petrolatum,
      (c) from about 5 to 25 weight % surface active detergent,
      (d) from about 1 to 10 weight % emulsifying agent,
      (e) from about 0 to 10 weight % humectant, and
      (f) from about 0 to 10 weight % silicone;
   wherein the emulsion is a liquid; and
   (2) wiping the emulsion from the peritoneum, thereby cleansing, moisturizing and leaving petrolatum as a protective barrier against wetness in one step.

8. The method of claim 7, wherein the surface active detergent is a mixture of triethanolamine laurylsulfate and cocoamphocarboxy glycinate.

9. The method of claim 7, wherein the emulsifying agent is a combination of behentrimonium metho sulfate, cetyl alcohol, stearyl alcohol and gylceryl monolaurate.

10. The method of claim 7, wherein the humectant is propylene glycol.

11. The method of claim 7, wherein the silicone is dimethicone.

12. The method of claim 7, wherein the surface active detergent is a mixture of triethanolamine laurylsulfate and cocoamphocarboxy glycinate;
   wherein the emulsifying agent is a combination of behentrimonium metho sulfate, cetyl alcohol, stearyl alcohol and gylceryl monolaurate;
   wherein the humectant is propylene glycol; and
   wherein the silicone is dimethicone.

13. The composition of claim 1, wherein fragrances, dyes, preservatives, emollients or other active ingredients are added.

14. The method of claim 7, wherein fragrances, dyes, preservatives, emollients or other active ingredients are added to the emulsion.

15. The method of claim 7, wherein the emulsion is applied by a pump spray.

16. The method of claim 7, wherein the emulsion is applied by a wipe.

17. The method of claim 7, wherein the emulsion is applied to a cloth and then applied to the peritoneum.

18. A composition for cleaning the peritoneum comprising an aqueous emulsion containing from about 10 to 50 weight t petrolatum, wherein the emulsion cleans, moisturizes, and leaves a petrolatum protective barrier when removed.

19. A method of cleaning the peritoneum comprising dispersion spraying the peritoneum with an aqueous emulsion containing from about 10 to 50 weight % petrolatum, and wiping the emulsion from the peritoneum with a clean cloth, wherein the emulsion cleans, moisturizes, and leaves a petrolatum protective barrier when removed.

* * * * *